United States Patent [19]

Dappen et al.

[11] Patent Number: 5,223,507
[45] Date of Patent: Jun. 29, 1993

[54] METHOD OF USING OPIOID COMPOUNDS AS DELTA OPIOID SELECTIVE AGONIST ANALGESICS

[75] Inventors: Michael S. Dappen, Gurnee; Barnett S. Pitzele, Skokie; Michael F. Rafferty, Buffalo Grove, all of Ill.

[73] Assignee: G. D. Searle & Co., Chicago, Ill.

[21] Appl. No.: 823,406

[22] Filed: Jan. 21, 1992

[51] Int. Cl.$^5$ ............................................. A61K 31/44
[52] U.S. Cl. ..................................................... 514/279
[58] Field of Search ................................. 514/282, 279

[56] References Cited

U.S. PATENT DOCUMENTS 4,816,586  3/1989  Portoghese .................... 544/340

OTHER PUBLICATIONS

Portoghese et al. Design of Peptidomimetic Delta Opioid Receptor etc. 33 1714-1720 Jan. 1990.
Portoghese et al. Application of the Message-Address Concept in etc. 31, No. 2 281-282 Jan. 1988.

*Primary Examiner*—Frederick E. Waddell
*Assistant Examiner*—Raymond J. Henley, III
*Attorney, Agent, or Firm*—Roberta L. Hastreiter; Paul D. Matukaitis

[57] ABSTRACT

The present invention provides a method for eliminating or ameliorating pain in an animal comprising administrating a therapeutically-effective amount of a substituted morphinoid compound of Formula I:

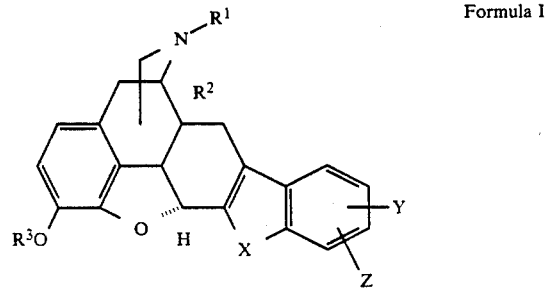

Formula I

The compounds are opioid agonists which are useful as analgesic agents for the treatment of pain.

3 Claims, No Drawings

METHOD OF USING OPIOID COMPOUNDS AS DELTA OPIOID SELECTIVE AGONIST ANALGESICS

BACKGROUND OF THE INVENTION (1) Field of the Invention

The present invention generally relates to compounds having pharmacological activity which are useful as pharmacological agents and, more particularly, as analgesic agents for the treatment of pain, to pharmaceutical compositions containing one or more of these compounds, and to methods of treatment employing these compounds. More particularly, the present invention concerns substituted morphinoid compounds, pharmaceutical compositions containing one or more of these compounds in combination with a pharmaceutically-acceptable carrier, and methods of treating pain employing these compounds.

Analgesic compounds are agents which alleviate pain without causing a loss of consciousness and, thus, which are useful for treating pain.

The major classes of analgesic compounds include narcotic analgesics, or opiates, compounds which alleviate pain and induce sleep, and analgesic-antipyretic compounds, compounds which alleviate pain and reduce fever, such as salicylates.

Although the efficacy of opiates in relieving pain is well established, the associated addiction liability of opiates is a distinct disadvantage of these compounds.

While salicylate and salicylate-like agents (nonsteroidal antiinflammatory agents or NSAIDS) are also efficacious in relieving pain, they often exhibit undesirable side effects, such as gastrointestinal irritation, as with aspirin, allergic response, as with aspirin, and/or liver toxicity with extended use, as with acetaminophen.

(2) Description of the Related Art

U.S. Pat. No. 4,816,586 issued Mar. 28, 1989, discloses delta opioid receptor antagonists of the

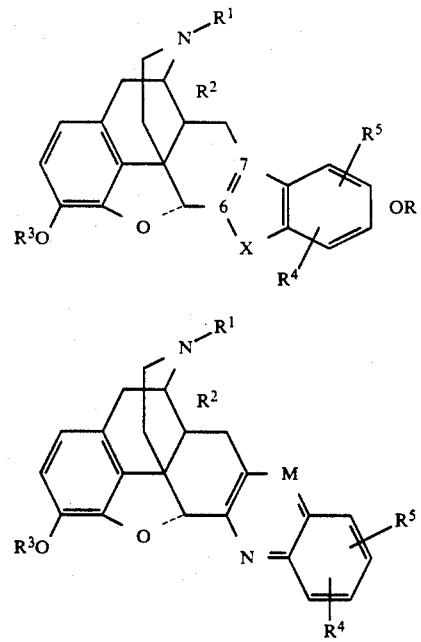

which are described as useful for blocking delta-opioid receptors in mammalian tissue by contacting the receptors with one of the delta-opioid antagonists of the noted formulae. The antagonists are suggested for use as pharmacologic and biochemical probes of opioid receptor structure and function and for use clinically, i.e., to counteract life-threatening shock.

SUMMARY OF THE INVENTION

This invention relates to compounds of the formula I

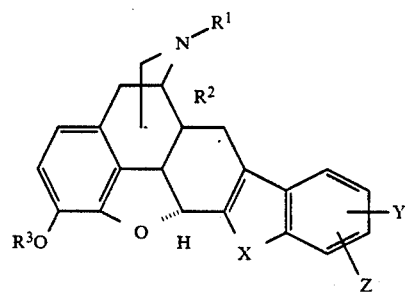

and pharmaceutically acceptable salts thereof, wherein $R^1$ represents hydrogen, $C_1$-$C_6$ alkyl, $C_3$-$C_6$ alkenyl, aralkyl or A-B wherein A represents $C_1$-$C_6$ alkylene and B represents $C_3$-$C_6$ cycloalkyl or substituted or unsubstituted aryl or heteroaryl;

$R^2$ represents hydrogen or $OR^4$ wherein $R^4$ represents hydrogen, $C_1$-$C_6$ alkyl

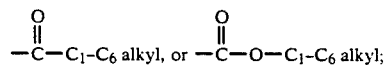

$R_3$ represents hydrogen, $C_1$-$C_6$ alkyl, aryl or aralkyl;

X is NR, O or S wherein R represents hydrogen or $C_1$-$C_6$ alkyl; and

Y and Z each independently represent hydrogen, halo, $C_1$-$C_6$ alkyl, $C_1$-$C_6$ alkoxy, $NO_2$ or $NH_2$, or Y and Z together form a phenyl ring, unsubstituted or substituted by one or more halo radicals or a pharmaceutically acceptable salt thereof.

DETAILED DESCRIPTION OF THE INVENTION

Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The term "lower alkyl" as used herein means a saturated hydrocarbon radical having from one to six carbon atoms, which can be a straight or branched chain. Representative of such radicals are methyl, ethyl, n-propyl, isopropyl, n-butyl, sec-butyl, isobutyl, tert-butyl and the like.

The term "aryl" as used herein means 5- and 6-membered single-ring aromatic radicals which may include from zero to four heteroatoms. Representative aryls include phenyl, thienyl, furanyl, pyridinyl, imidazolyl, thiazolyl, pyrimidinyl, pyrazinyl, pyridazinyl, (is)oxazolyl, triazolyl, tetrazolyl, pyrrolyl, pyridinyl-N-oxide and the like.

The term "flash chromatography" as used herein is described in J. Org. Chem. 1978, 43,2923.

The term "analgesia" as used herein means the reduction, or absence, of sensibility to pain, designating particularly the relief of pain without loss of consciousness.

The term "animal" as used herein includes humans and animals.

The term "composition" as used herein means a product which results from the combining of more than one ingredient.

The phrase "ED$_{50}$ dose" as used herein means that dose of a compound or drug which produced a defined biological effect, such as producing analgesia, in 50% of the animals to which the compound or drug was administered.

The abbreviation "i.g." as used herein means that a compound or drug was administered intragastrically, as defined below.

The term "intragastrically" as used herein means that a compound or drug was administered into the stomach.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, valerate, oleate, palmitate, stearate, laurate, benzoate, lactate, phosphate, tosylate, citrate, maleate, fumarate, succinate, tartrate, napsylate, clavulanate and the like salts and alkali metal salts such as sodium and potassium and alkaline earth salts, such as calcium and magnesium.

The term "phenyl" as used herein means the group $C_6H_5$—, derived from benzene.

The abbreviation "s.c." as used herein means that a compound or drug was administered subcutaneously.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

Description of Invention

In one aspect, the present invention provides compounds comprising a structure of Formula I, as described above, and pharmaceutically-acceptable salts, esters and amides thereof.

The compounds of the present invention comprise a class of substituted morphinoid compounds which compounds have been shown to exhibit activity as opioid agonists.

Specific compounds within the scope of the invention include, but are not limited to, the compounds discussed in the examples presented below, as well as their pharmaceutically-acceptable salts, esters, and amides.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of the present invention may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," *J. Pharm. Sci.,* 66:1-19 (1977).)

In other cases, the compounds of the invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. The pharmaceutical compositions of the invention may be specially formulated for oral administration in solid or liquid form, for parenteral injection, or for rectal or vaginal administration.

In yet a further aspect, the present invention provides a method for eliminating or ameliorating pain in an animal, comprising administering a therapeutically-effective amount of a compound of Formula I, as described hereinabove, to the animal.

(3) Utility

Compounds of the present invention exhibit activity as opioid agonist analgesics.

Compounds within the present invention, and the pharmaceutical compositions comprising one or more of these compounds, are useful as analgesic agents for the elimination or amelioration of pain in animals.

(4) Methods of Preparation

In general, the compounds of the present invention may be prepared by the methods illustrated in the following general reaction schemes, or by modifications thereof, using readily-available starting materials, reagents and conventional synthesis procedures. Unless otherwise specified, the various substituents of the compounds and materials present in the general reaction schemes are defined in the same manner as they are defined above in Formula I.

If a particular enantiomer of a compound of the present invention is desired, one could start with the desired enantiomer of the starting material, or it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The compounds of this invention may be prepared by the methods illustrated in the following reaction schemes.

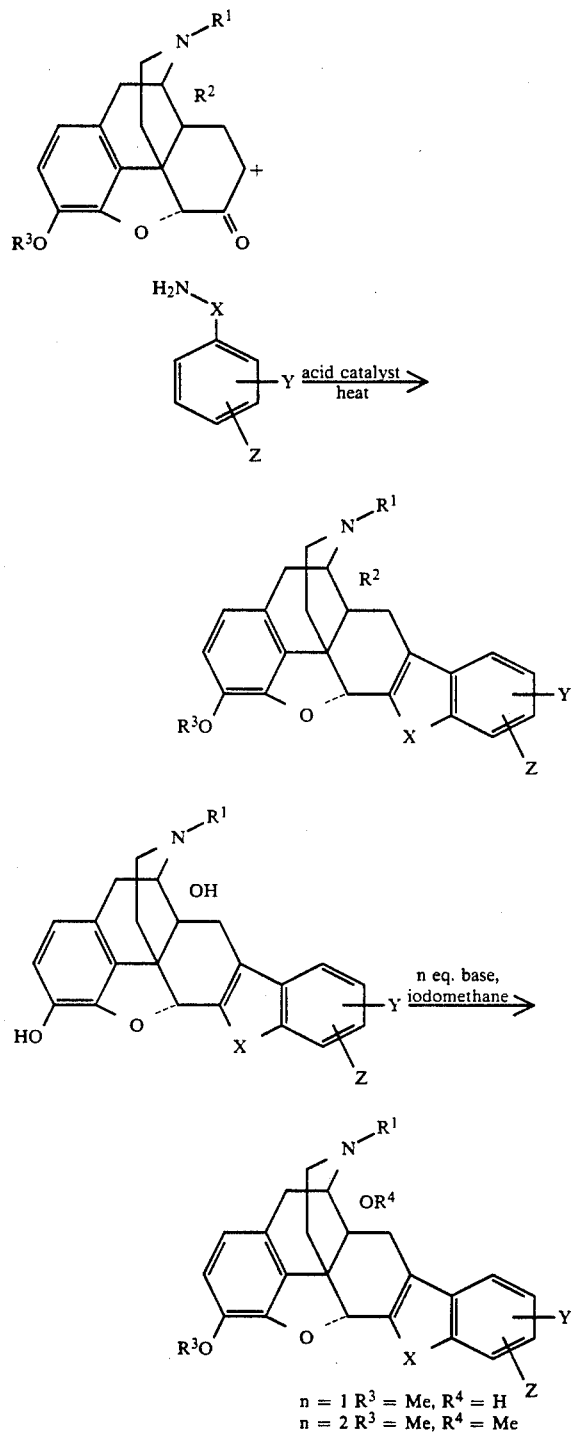

While the various aspects of the present invention are described herein with some particularity, those of skill in the art will recognize numerous modifications and variations which remain within the spirit of the invention. These modifications and variations are within the scope of the invention as described and claimed herein.

EXAMPLES

The following examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

In the examples, all parts are by weight unless otherwise indicated.

All starting materials employed in the examples are commercially available. Most of the starting materials were obtained from Aldrich Chemical Co., Milwaukee, Wisconsin or Mallinckrodt Chemical, St. Louis, Mo.

All patents and publications referred to in the examples, and throughout the specification, are hereby incorporated herein by reference, without admission that such is prior art.

EXAMPLE I 5,6,7,8,14,14b$\beta$-Hexahydro-7-methyl-4,8(R,$\alpha$)-methano-4bS*-benzofuro[2,3-a]pyrido[4,3-b]carbazole-1, 8a$\beta$(9H)-diol, monohydrochloride (compound 1)

A mixture of oxymorphone hydrochloride (1.99 g, 5.89 mmol) and phenylhydrazine hydrochloride (1.70 g, 11.8 mmol) was slurried in glacial acetic acid (30 mL) and heated to reflux for 6 h. The mixture was cooled to room temperature and the resulting precipitated solid was collected by filtration and washed with ether. The material was recrystallized from methanol to yield a tan solid. $^1$H NMR (DMSO-d$_6$) $\delta$9.29 (br s, 2H), 7.33 (comp m, 2H), 7.10 (t, J=7 Hz, 1 H), 6.96 (t, J=7 Hz, 1H), 6.67 (d, J=8 Hz, 1H), 6.60 (d, J=8 Hz, 1 H), 5.68 (s, 1 H), 3.84 (br d, J=7 Hz, 1 H), 3.50–3.10 (comp m, 3 H), 2.94–2.45 (comp m, 4 H), 2.88 (s, 3 H), 1.78 (m, 1 H).

EXAMPLE II 6,7,8,14b$\beta$-Tetrahydro-7-methyl-4,8(R,$\alpha$)-methano-4bS*-5H-bisbenzofuro[3,2-e:2',3'-g]isoquinoline-1, 8a$\beta$(9H)-diol, monohydrochloride (compound 2)

A mixture of oxymorphone hydrochloride (10.00 g, 29.60 mmol) and O-phenylhydroxylamine hydrochloride (4.37 g, 30.0 mmol) was slurried in absolute ethanol (150 mL) and then treated with methanesulfonic acid (2.88 g, 30.0 mmol). The mixture was then heated to reflux for 20 h before cooling to room temperature. The solvent was removed by rotary evaporation, and the residue was taken up in 1 N aqueous ammonium hydroxide (200 mL). The solution was extracted with ethyl acetate (2×50 mL), and the combined ethyl acetate extracts were washed with water (100 mL), dried (Na$_2$SO$_4$), then evaporated in vacuo to give the free base of 2. The free base was taken up in isopropyl alcohol (50 mL) and treated with a 1:1 mixture of 12 N hydrochloric acid in isopropyl alcohol (10 mL). A large excess of ether was added to precipitate the hydrochloride salt which was collected by filtration and then recrystallized from methanol/ether to give the title compound as a tan solid. $^1$H NMR (DMSO-d$_6$) $\delta$9.37 (br s, 2 H), 7.61 (d, J=8 Hz, 1 H), 7.50 (d, J=8 Hz, 1 H), 7.37 (t, J=8 Hz, 1 H), 7.26 (t, J=8 Hz, 1 H), 6.66 (comp m, 2 H), 5.77 (s, 1 H), 3.91 (d, J=7 Hz, 1 H), 3.51–3.10 (comp m, 3 H), 2.97–2.50 (comp m, 3 H), 2.89 (d, J=4 Hz, 3 H), 1.81 (d, J=12 Hz, 1 H).

EXAMPLE III 5,6,7,8,16, 16b$\beta$-Hexahydro-7-methyl-4,8(R,$\alpha$)-methano-4BS*-benzo[i]benzofuro[2,3-a]pyrido[4,3-b]carbazole-1,8a$\beta$(9H)-diol, monohydrochloride (compound 3)

The title compound was prepared by the method described in example I except that $\alpha$-napthylhydrazine hydrochloride was used in place of the phenylhydrazine hydrochloride. $^1$H NMR (DMSO-d$_6$) $\delta$9.30 (br s, 2 H), 8.45 (d, J=9 Hz, 1 H), 7.90 (d, J=9 Hz, 1 H), 7.58–7.39 (comp m, 4 H), 6.68 (d, J=8 Hz, 1 H), 6.6I (d, J=8 Hz, 1 H), 6.40 (br s, 1 H), 5.79 (s, 1 H), 4.14 (br s, 1 H), 3.88 (br d, J=7 Hz, 1 H), 3.51–2.50 (comp m, 6 H), 2.90 (s, 3 H), 1.82 (br d, J=13 H, 1 H).

EXAMPLE IV 2 6,7,8,14b$\beta$-Hexahydro-1,8a$\beta$-(9H)-dimethoxy-7-methyl-4,8(R,$\alpha$)-methano-4bS*-5H-bisbenzofuro[3,2-e:2',3'-g]isoquinoline (compound 4)

Potassium hydride, as a 35% dispersion in oil (462 mg dispersion, 4.05 mmol KH) was washed with hexane (3×10 mL) to remove the oil and then suspended in tetrahydrofuran (THF, 5 mL). The free base of compound 2 (507 mg, 1.35 mmol) as a solution in THF (20 mL) was added dropwise via cannula. The mixture was stirred for 25 min at room temperature before the addition of iodomethane (979 mg, 6.75 mmol).

The resulting cloudy mixture was stirred for 20 min before treating with a saturated aqueous ammonium chloride solution (10 mL). The mixture was poured into 1 N aqueous ammonium hydroxide (100 mL) and extracted with ethyl acetate (2×100 mL). The combined organic extracts were dried (Na$_2$SO$_4$), then filtered and evaporated in vacuo to give an oily residue which was recrystallized from chloroform/isopropyl ether to give the title compound as a white solid. $^1$H NMR (CDCl$_3$) $\delta$7.46 (d, J=8 Hz, 1 H), 7.38 (d, J=8 Hz, 1 H), 7.27 (t, J=8 Hz, 1 H), 7.17 (t, J=8 Hz, 1 H), 6.64 (comp m, 2 H), 5.63 (s, 1 H), 3.78 (s, 3 H), 3.36 (d, J=18 Hz, 1 H), 3.23 (s, 3 H), 3.03 (d, J=17 Hz, 1 H), 2.72–2.26 (comp m, 6 H), 2.51 (br s, 3 H), 1.72 (m, 1 H).

EXAMPLE V 6,7,8,14b$\beta$-Tetrahydro-1-methoxy-7-methyl-4,8(R,$\alpha$)-methano-4bS*-5H-bisbenzofuro[3,2-e:2',3'-g]isoquinolin-8a$\beta$(9H)-ol (compound 5)

Sodium hydride, as a 60% dispersion in oil (213 mg dispersion, 5.33 mmol) was washed with pentane (10 mL) to remove the oil and then suspended in dimethylformamide (DMF, 20 mL) and cooled in an ice bath. The free base of compound 2 (2.00 g, 5.33 mmol) was added in one portion and the mixture was stirred for 25 min before addition of iodomethane (2.31 g, 16.0 mmol). The mixture was stirred for 45 min at 0° C. and 45 min at room temperature and then poured into 1 N aqueous ammonium hydroxide (50 mL). The cloudy solution was extracted with ethyl acetate (2×50 mL) and the combined organic extracts were washed with water (50 mL), then dried (Na$_2$SO$_4$), filtered and evaporated in vacuo to give the crude product. The product was purified by silica gel chromatography, eluting with 4% methanol in methylene chloride to give the title compound as a white solid. $^1$H NMR (CDCl$_3$) δ7.44 (d, J=8 Hz, 1 H), 7.38 (d, J=8 Hz, 1 H), 7.25 (t, J=8 Hz, 1 H), 7.16 (t, J=8 Hz, 1 H), 6.65 (comp m, 2 H), 5.61 (s, 1 H), 3.78 (s, 3 H), 3.26 (d, J=18 Hz, 1 H), 3.04 (d, J=7 Hz, 1 H), 2.92 (d, J=18 Hz, 1 H), 2.82–2.28 (comp m, 6 H), 2.42 (s, 3 H), 1.83 (m, 1 H).

EXAMPLE VI 11,13-Dibromo-5,6,7,8,14,14bβ-hexahydro-7-methyl-4,8(R,α)-methano-4bS*-benzofuro[2,3-a]pyrido[4,3-b] carbazole-1,8aβ(9H)-diol, monohydrochloride (compound 6)

A mixture of oxymorphone hydrochloride (504 mg, 1.49 mmol) and 2,4-dibromophenylhydrazine hydrochloride (0.90 g, 3.0 mmol) was slurried in glacial acetic acid (10 mL) and heated to reflux for 6 h. The mixture was cooled to room temperature and the resulting precipitated solid was collected by filtration and washed with ether. The solid was taken up in 1 N aqueous ammonium hydroxide (25 mL) and the mixture was extracted with chloroform (2×25 mL). The combined organic extracts were evaporated in vacuo and the residue was purified by silica gel chromatography, eluting with 10% methanol in methylene chloride to give the free base of the title compound. The free base was converted to its hydrochloride salt by dissolution in isopropyl alcohol and addition of hydrogen chloride. $^1$H NMR (DMSO-d6) δ11.9 (br s, 1 H), 9.42 (br s, 1 H), 9.37 (br s, 1 H), 7.60 (s, 1 H), 7.51 (s, 1 H), 6.69 (d, J=8 Hz, 1 H), 6.53 (d, J=8 Hz, 1 H), 6.42 (br s, 1 H), 5.66 (s, 1 H), 3.84 (d, J=7 Hz, 1 H), 3.46 (d, J=18 Hz, 1 H), 3.20–3.10 (comp m, 2 H), 2.89 (d, J=5 Hz, 3 H), 2.90–2.42 (comp m, 4 H), 1.80 (br d, J=14 Hz, 1 H).

EXAMPLE VII

13-Bromo-5,6,7,8,14bβ-hexahydro-7-methyl-4,8(R,α)-methano-4bS*-benzofuro[2,3-a]pyrido [4,3-b]carbazole-1,8aβ(9H)-diol, monohydrochloride (compound 7)

The title compound was prepared by the method described in example VI except that 2-bromophenylhydrazine hydrochloride was used in place of the 2,4-dibromophenylhydrazine hydrochloride. For the free base of the title compound: $^1$H NMR (CDCl$_3$) δ8.54 (br s, 1 H), 7.32 (d, J=8 Hz, 1 H), 7.24 (d, J=8 Hz, 1 H), 6.88 (t, J=8 Hz, 1 H), 6.63 (d, J=8 Hz, 1 H), 6.55 (d, J=8 Hz, 1 H], 5.69 (s, 1 H), 3.22 (d, J=18 Hz, 1 H), 3.02 (d, J=7 Hz, 1 H), 2.83 (d, J=16 Hz, 1 H), 2.78 (dd, J=7, 18 Hz, 1 H), 2.61 (d, J=16 Hz, 1 H), 2.53–2.30 (comp m, 2 H), 2.43 (s, 3 H), 1.78 (d, J=11 Hz, 1 H).

EXAMPLE VIII 5,6,7,8,14,14bβ-Hexahydro-7(2-propenyl)-4,8 (R,α)-methano-4bS*-benzofuro[2,3-a]pyrido[4,3-b] carbazole-1,8aβ(9H)-diol, monohydrochloride (compound 8)

The title compound was prepared as described in example VI except that naloxone hydrochloride was used in place of the oxymorphone hydrochloride and phenylhydrazine hydrochloride was used in place of 2,4dibromophenylhydrazine hydrochloride. For the free base of the title compound: $^1$H NMR (CDCl$_3$) δ8.28 (br s, 1 H), 7.40 (d, J=8 Hz, 1 H), 7.25 (d, J=8 Hz, 1 H), 7.12 (t, J=8 Hz, 1 H), 7.01 (t, J=8 Hz, 1 H), 6.57 (d, J=8 Hz, 1 H), 6.49 (d, J=8 Hz, 1 H), 5.85 (m, 1 H), 5.60 (s, 1 H), 5.26–5.17 (comp m, 2 H), 3.20–3.11 (comp m, 3 H), 2.89 (d, J=16 Hz, 1 H), 2.78 (dd, J=7,18 Hz, 1 H), 2.67–2.58 (comp m, 2 H), 2.31 (comp m, 2 H), 1.77 (d, J=12 Hz, 1 H).

EXAMPLE IX 6,7,8,14β-Tetrahydro-7-(2-propenyl)-4,8(R,α)-methano-4bS*-5H-bisbenzofuro[3,2-e:2',3'-g] isoquinoline-1,8aβ(9H)-diol, monohydrochloride (compound 9)

The title compound was prepared as described in example II except that naloxone hydrochloride was used in place of the oxymorphone hydrochloride $^1$H NMR (DMSO-d$_6$) δ9.37 (br s, 2 H), 7.61 (d, J=8 Hz, 1 H), 7.46 (d, J=8 Hz, 1 H), 7.36 (t, J=8 Hz, 1 H), 7.28 (t, J=8 Hz, 1 H), 6.66 (comp m, 2 H), 6.58 (s, 1 H), 5.92 (m, 1 H), 5.67–5.51 (comp m, 2 H), 3.88–3.75 (comp m, 2 H), 3.50 (d, J=18 Hz, 1 H), 3.45–3.10 (comp m, 2 H), 2.96 (d, J=12 Hz, 1 H), 2.80–2.55 (comp m, 2 H), 1.83 (d, J=12 Hz, 1 H).

EXAMPLE X

13-Bromo-5,6,7,8,14, 14bβ-hexahydro-7-(2-propenyl)-4,8(R,α)-methano-4bS*-benzofuro [2,3-a]pyrido[4,3-b]carbazole-1,8aβ(9H)-diol monohydrochloride (compound 10)

The title compound was prepared as described in example VI except that naloxone hydrochloride was used in place of the oxymorphone hydrochloride and 2-bromophenylhydrazine hydrochloride was used in place of 2,4-dibromophenylhydrazine hydrochloride. For the free base of the title compound: $^1$H NMR (CDCl$_3$) δ8.43 (br s, 1 H), 7.32 (d, J=8 Hz, 1 H), 7.25 (d, J=8 Hz, 1 H), 6.88 (t, J=8 Hz, 1 H), 6.63 (d, J=8 Hz, 1 H), 6.56 (d, J=8 Hz, 1 H), 5.84 (m, 1 H), 5.69 (s, 1 H), 5.28–5.18 (comp m, 2 H), 3.22–3.11 (comp m, 4 H), 2.83 (d, J=18 Hz, 1 H), 2.80 (dd, J=7, 18 Hz, 1 H), 2.66–2.58 (comp m, 2 H), 2.33 (comp m, 2 H), 1.69 (m, 1H).

EXAMPLE XI 6,7,8,8a,9,14bβ-Hexahydro-7-methyl-4,8(R,α)-methano-4bs*-5H-bisbenzofuro[3,2-e:2',3'-g] isoquinolin-1-ol, monohydrochloride (compound 11)

The title compound was prepared as described in example II except that dihydromorphinone hydrochloride was used in place of the oxymorphone hydrochloride. For the free base of the title compound: $^1$H NMR (CDCl$_3$) δ7.45 (d, J=8 Hz, 1 H), 7.38 (d, J=8 Hz, 1 H), 7.28 (t, J=8 Hz, 1 H), 7.19 (t, J=8 Hz, 1 H), 6.67 (d, J=8 Hz, 1 H), 6.59 ( d, J=8 Hz, 1 H), 5.61 (s, 1 H), 3.39 (m, 1 H), 3.09 (d J=18 Hz, 1 H), 2.76–1.95 (comp m, 2 H), 2.46 (s, 3H).

EXAMPLE XII 5,6,7,8,8a,9,14, 14bβ-Octahydro-7-methyl-4,8(R,α)-methano-4bS*-benzofuro[2,3-a] pyrido[4,3-b]carbazol-1-ol, monohydrochloride (compound 12)

The title compound was prepared as described in example VI except that dihydromorphinone hydrochloride was used in place of the oxymorphone hydrochloride and phenylhydrazine hydrochloride was used in place of 2,4-dibromophenylhydrazine hydrochloride. The free base of the title compound was recrystallized from ethanol before conversion to its hydrochloride salt. $^1$H NMR (DMSO-d$_6$) δ11.30 (br s, 1H), 9.18 (br s, 1 H), 7.37 (comp m, 2 H), 7.09 (t, J=8 Hz, 1 H), 6.94 (t, J=8 Hz, 1 H), 6.61 (comp m, 2 H), 5.79 (s, 1 H), 3.35-3.20 (comp m, 2 H), 3.07-2.98 (comp m, 2 H), 2.87 (d, J - 3 Hz, 3 H), 2.80-2.70 (comp m, 3 H), 2.35 (m, 1 H), 1.95 (m, 2 H).

EXAMPLE XIII

13-Bromo-5,6,7,8,8a,9,14,14bβ-octahydro-7-methyl-4,8(R,α)-methano-4bS*-benzofuro [2,3-a]pyrido[4,3-b]carbazol-1-ol, monohydrochloride (compound 13)

The title compound was prepared as described in example VI except that dihydromorphinone hydrochloride was used in place of the oxymorphone hydrochloride and 2-bromophenylhydrazine hydrochloride was used in place of 2,4-dibromophenylhydrazine hydrochloride. $^1$H NMR (DMSO-d$_6$) δ11.55 (br s, 1 H), 9.21 (br s, 1 H), 7.39 (d J=8Hz, 1 H), 7.32 (d, J=8 Hz, 1 H), 6.92 (t, J=8 Hz, 1 H), 6.62 (comp m, 2 H), 5.76 (s, 1 H), 3.30-1.88 (comp m, 10 H), 2.85 (br s, 3 H).

EXAMPLE XIV 6,7,8,14bβ-Tetrahydro-7-propyl-4,8(R,α)-methano-4bS*-5H-bisbenzofuro[3,2-e:2',3'-g] isoquinoline-1,8aβ(9H)-diol, monohydrochloride (compound 14)

An ethanolic solution of 6,7,8,14bβ-tetrahydro-7-(2-propenyl)-4,8(R,α)-methano-4bS*-5H-bisbenzofuro[3-,2e:2',3'-g]isoquinoline-1,8aβ(9H)-diol, monohydrochloride (compound 9) (328 mg, 0.749 mmol) Was hydrogenated over 4% palladium on carbon (5 p.s.i. overpressure H$_2$) for 8 h at room temp. The solution was filtered and the solvent evaporated in vacuo to give a residue which was recrystallized from methanol/ethyl acetate to give compound 14 as a white solid. $^1$H NMR (DMSO-d$_6$) δ9.37 (s, 1 H), 9.01 (br s, 1 H), 7.62 (d J=8 Hz, 1 H), 7.47 (d, J=8 Hz, 1 H), 7.38 (t, J=8 Hz, 1 H), 7.27 (t, J=8 Hz, 1 H), 6.64 (comp m, 2 H), 5.77 (s, 1 H), 3.93 (br d, J=6 Hz, 1 H), 3.45-2.50 (9 H), 1.73-1.56 (3 H), 0.96 (t, J=7 Hz, 3 H).

EXAMPLE XV 6,7,8,14bβ-Tetrahydro-7-(cyclobutylmethyl)-4,8 (R,α)-methano-4bS*-5H-bisbenzofuro [3,2-e:2',3'-g]isoquinoline-1,8aβ(9H)-diol, monohydrochloride (compound 15)

6,7,8,14bβ-Tetrahydro-4,8(R,α)-methano-4bS*-5H-bisbenzofuro[3,2-e:2',3'-g]isoquinoline-1,8aβ(9H)-diol (260 mg, 0.720 mmol) was slurried in dimethylformamide (DMF, 3 mL). Triethylamine (218 mg, 2.16 mmol) was added, followed by a solution of cyclobutanecarbonyl chloride (213 mg, 1.80 mmol) in DMF (2 mL). After stirring for 4 h, the mixture was poured into 1 N aq HCl (25 mL) and the mixture was extracted with ethyl acetate (2×25 mL). The combined organic extracts were washed with 1 N aq NH$_4$OH, then the solvent was evaporated in vacuo to give the intermediate cyclobutyl amide as an oily residue.

The residue was taken up in THF (5 mL) and treated with lithium aluminum hydride (55 mg, 1.44 mml). The resulting slurry was stirred for 2 h before cooling in an ice bath. The mixture was treated, in succession, with water (0.06 mL), 10% aq NaOH (0.6 mL), and water (0.18 mL) and stirred for 0.5 h. The mixture was poured into 1 N aq HCl (25 mL) and the solution was washed with ethyl acetate (2×25 mL). The aqueous phase was made basic with conc. aq NH$_4$OH and extracted with ethyl acetate (3×25 mL). The combined organic extracts were dried (Na$_2$SO$_4$), filtered, then evaporated in vacuo to give a residue which was purified by silica gel chromatography (eluting with 5% methanol in methylene chloride) to give the free base of the title compound. The free base was taken up in ethanol (ca. 2 mL) and treated with a 7 M hydrogen chloride solution in dioxane (0.1 mL). The hydrochloride salt was precipitated by addition of excess ether to give the title compound as a white solid. For the free base of the title compound: $^1$H NMR (CDCl$_3$) δ7.41 (comp m, 2 H), 7.27 (t, J=8 Hz, 1 H), 7.18 (t, J=8 Hz, 1 H), 6.62 (d, J=8 Hz, 1 H), 6.56 (d, 8 Hz, 1 H), 5.58 (s, 1 H), 3.20 (d, J=18 Hz, 1 H), 3.09 (d, J=7 Hz, 1 H), 2.84-2.75 (comp m, 2 H), 2.62-1.70 (14 H).

EXAMPLE XVI 6,7,8,14bβ-Tetrahydro-7-(2-furanylmethyl)-4,8 (R,α)-methano-4bS*-5H-bisbenzofuro [3,2-e:2',3'-g]isoquinoline-i,8aβ(9H)-diol, monohydrochloride (compound 16)

6,7,8,14bβ-Tetrahydro-4,8(R,α)-methano-4bS*-5H-bisbenzofuro[3,2-e:2',3'-g]isoquinoline-1, 8aβ(9H)-diol (165 mg, 0.459 mmol) was slurried in methanol (5 mL). Glacial acetic acid (41 mg, 0.69 mmol) was added, followed by furfural (53 mg, 0.55 mmol) and sodium cyanoborohydride (57 mg, 0.91 mmol). The mixture was stirred at room temp for 21 h before addition of 6 N HCl (5 mL). After the gas evolution subsided, the mixture was stirred for 20 min before rotary evaporation to remove methanol. The residue was diluted with water (25 mL) and then extracted with ether (2×25 mL)J to remove neutral organics. The aqueous phase was made basic with conc. aq NH$_4$OH and then extracted with ethyl acetate (2×25 mL). The combined organic extracts were dried (Na$_2$SO$_4$), filtered, then evaporated in vacuo to give a residue which was purified by silica gel chromatography (eluting with 5% methanol in methylene chloride) to give the free base of the title compound. The free base was taken up in ethanol (ca. 2 mL) and treated with a 7 M hydrogen chloride solution in dioxane (0.10 mL). The hydrochloride salt was precipitated by addition of excess ether to give the title compound as a tan solid. For the free base of the title compound: $^1$N NMR (CDCl$_3$/CD$_3$OD) δ7.43 (m, 1 H), 7.39 (comp m, 2 H), 7.27 (dt, J=2, 8 Hz, 1 H), 7.16 (t, J=8 Hz, 1 H), 6.64 (d, J=8 Hz, 1 H), 6.58 (d, J=8 Hz, 1 H), 6.38, (m, 1 H), 6.29 (m, 1 H), 5.61 (s, 1 H), 3.73 (br s, 2 H), 3.23 (d, J=16 Hz, 1 H), 3.10 (d, J=7 Hz, 1 H), 2.88-2.44 (comp m, 6 H), 2.78 (d, J=15 Hz, 1 H), 2.59 (dt, J=2, 15 Hz, 1 H), 1.83 (m, 1 H).

EXAMPLE XVII 5,6,7,8,14,14bβ-Hexahydro-7-methyl-4,8 (R,α)-methano-4bS*-benzofuro[2,3-a] pyrido[4,3-b]carbazole-1,8aβ(9H)-diol, 1-acetate (compound 17)

5,6,7,8,14,14bβ-Hexahydro-7-methyl-4,8(R,α)-methano-4bS*-benzofuro[2,3-a]pyrido[4,3-b]carbazole-1, 8aβ-9H)-diol monohydrochloride (compound 1) (1.00 g, 2.43 mmol) was dissolved in a mixture of pyridine (5 mL) and acetic anhydride (10 mL) and stirred for 23 h at room temp. The solvents were removed via rotary evaporation and the residue treated with methanol (30 mL) and satd aq sodium bicarbonate (15 mL). After stirring for 1.5 h, the methanol was removed by rotary evaporation and the residue slurried in water (60 mL). The mixture was extracted with chloroform (2×50 mL) and the combined organic extracts were dried (Na₂SO₄), filtered, then evaporated in vacuo. The resulting residue was recrystallized from chloroform/ethyl acetate to give the title compound as a white solid. ¹H NMR (CDCl₃) δ8.17 (s, 1 H), 7.43 (d, J=2, 8 Hz, 1 H), 7.31 (d, J=2, 8 Hz, 1 H), 7.17 (dt, J=1, 8 Hz, 1 H), 7.05 (t, J=8 Hz, 1 H), 6.79 (d, J=8 Hz, 1 H), 6.67 (d, J=8 Hz, 1 H), 5.72 (s, 1 H), 3.29 (d, J=18 Hz, 1 H), 3.10 (d, J=7 Hz, 1 H), 2.92 (d, J=15 Hz, 1 H), 2.86 (dd, J=7, 18 Hz, 1 H), 2.65 (d, J=15 Nz, 1 H), 2.56-2.29 (3H), 2.46 (s, 3 H), 2.26 (s, 3 H), 1.86 (m, 1 H).

EXAMPLE XVIII 5,6,7,8,14,14bβ-Hexahydro-7-methyl-4,8(R,α)-methano-4bS*-benzofuro[2,3-a]pyrido[4,3-b]carbazole-1,8aβ-9H)-diol, diacetate, monohydrochloride (compound 18)

The mother liquor from the recrystallization of compound 17 was concentrated to provide a residue containing compound 17 and the free base of compound 1. The residue was dissolved in a mixture of pyridine (5 mL) and acetic anhydride (5 mL) and stirred for 17 h at room temp and 3 h at reflux temperature. The solvents were removed via rotary evaporation and the residue treated with methanol (30 mL) and satd aq sodium bicarbonate (15 mL). After stirring for 1.5 h, the methanol was removed by rotary evaporation and the residue slurried in water (60 mL). The mixture was extracted with chloroform (2×50 mL) and the combined organic extracts were dried (Na₂SO₄), filtered, then evaporated in vacuo. The resulting residue was purified b silica gel chromatography (eluting with 5% methanol in methylene chloride) to give the free base of the title compound. The free base was taken up in ethanol (ca. 2 mL) and treated with a 7 M hydrogen chloride solution in dioxane (0.10 mL). The hydrochloride salt was precipitated by addition of excess ether to give the title compound as a white solid. ¹H NMR (DMSO-d₆) δ10.12 (br s, 1 H), 7.32 (comp m, 2H), 7.11 (t, J=8 Hz, 1 H), 6.93 (comp m, 2 H), 6.82 (d, J=8 Hz, 1 H), 5.97 (s. 1 H), 4.93 (br d, J=7 Hz, 1 H), 3.77 (d, J=16 Hz, 1 H), 3.68 (d, J=19 Hz, 1 H), 3.50-3.25 (3 H), 2.99 (d, J=5 Hz, 3 H), 2.90-2.55 (3 H), 2.21 (s, 3 H), 1.94 (s, 3 H), 1.90 (m, 1 H).

EXAMPLE XIX 5,6,7,8,14,14bβ-Hexahydro-7-methyl-4,8(R,α-methano-4bS*-benzofuro[2,3-a]pyrido[4,3-b]carbazole-1,8aβ-9H)-diol,8a-acetate monohydrochloride (compound 19)

5,6,7,8,14,14bβ-Hexahydro-7-methyl-4,8(R,α)-methano-4bS*-benzofuro[2,3-a]pyrido[4,3-b]carbazole-1, 8aβ-9H)-diol, diacetate (free base of compound 18) (256 mg, 0.558 mmol) was slurried in ethanol (6 mL) and powdered sodium hydroxide (25 mg, 0.61 mmol) was added. After stirring the homogeneous mixture for 3.5 h, the ethanol was removed by rotary evaporation and the residue was taken up into water (25 mL). The aqueous solution was extracted with ether (2×25 mL) and then made acidic with 1 N aq NCl. The acidic solution was then made basic with conc. aq NH₄OH and extracted with ethyl acetate (2×25 mL). It was discovered that the ether extracts contained most of the material, thus the ether and ethyl acetate extracts were combined and evaporated in vacuo. The resulting residue was purified by silica gel chromatography, eluting with 5% methanol in methylene chloride to give the free base of the title compound. The free base was taken up in ethanol (ca. 3 mL) and treated with a 7 M hydrogen chloride solution in dioxane (0.10 mL). The hydrochloride salt was precipitated by addition of excess ether to give the title compound as a white solid. For the free base of the title compound: ¹H NMR (CDCl₃) δ7.39 (d, J=2, 8 Hz, 1 H), 7.35 (d, J=2, 8 Hz, 1 H), 7.15 (dt, J=1, 8 Hz, 1 H), 7.02 (t, J=8 Hz, 1 H), 6.56 (ab q, J=8 Hz, 2 H), 5.65 (s, 1 H), 4.41 (d, J=7 Hz, 1 H), 3.76 (d, J=16 Nz, 1 H), 3.29 (d, J=18 Hz, 1 H), 2.72 (dd, J=7, 18 Hz, 1 H), 2.59 (d, J=16 Hz, 1 H), 2.55-2.32 (3H), 2.40 (s, 3 H), 1.96 (s, 3 H), 1.75 (m, 1 H).

TABLE I

| Cmpd No. | Structure | Molecular Formula | Microanalysis | | Optical Rotation [α]$_D$ |
|---|---|---|---|---|---|
| | | | Calcd | Found | |
| 1 | (structure) | C₂₃H₂₃N₂O₃Cl + 0.6 H₂O | C 65.51<br>H 5.78<br>N 6.64 | 65.40<br>5.87<br>6.54 | −450.8° |
| 2 | (structure) | C₂₃H₂₂NO₄Cl + 1.0 H₂O | C 64.26<br>H 5.59<br>N 3.26 | 64.44<br>5.63<br>3.32 | −373.7° |

TABLE I-continued

| Cmpd No. | Structure | Molecular Formula | Microanalysis Calcd | Found | Optical Rotation $[\alpha]_D$ |
|---|---|---|---|---|---|
| 3 | 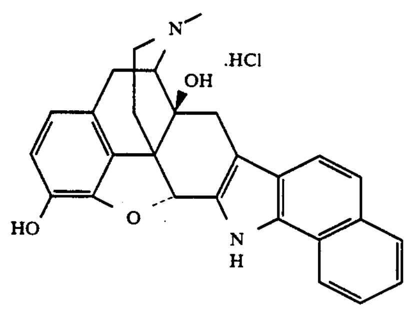 | $C_{27}H_{25}N_2O_3Cl$ + 1.0 $H_2O$ · HCl | C 67.70<br>H 5.68<br>N 5.85 | 67.42<br>5.93<br>5.57 | −766.6° |
| 4 | 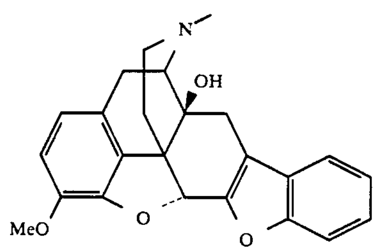 | $C_{25}H_{25}NO_4$ + 0.35 $CHCl_3$ | C 68.38<br>H 5.47<br>N 3.18 | 68.71<br>5.94<br>3.08 | −431.5° |
| 5 | 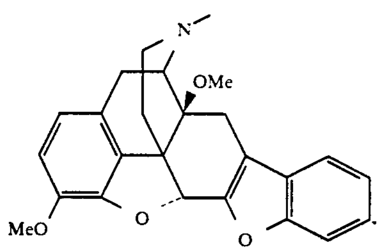 | $C_{24}H_{23}NO_4$ + 0.7 $H_2O$ | C 71.69<br>H 6.12<br>N 3.48 | 71.78<br>5.83<br>3.49 | |
| 6 | 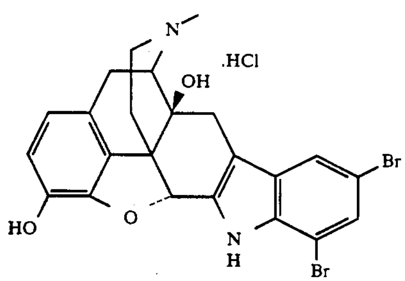 | $C_{23}H_{20}N_2O_3Br_2Cl$ · HCl | C 48.66<br>H 3.55<br>N 4.93 | 48.61<br>3.89<br>4.82 | −439.3° |
| 7 | 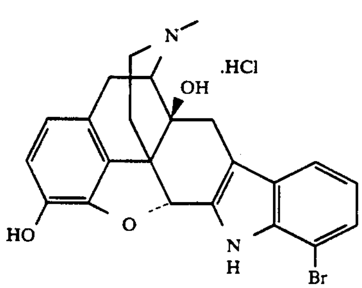 | $C_{23}H_{22}N_2O_3BrCl$ + 0.9 $H_2O$ · HCl | C 54.59<br>H 4.74<br>N 5.54<br>Cl 7.01<br>Br 15.79 | 54.60<br>4.52<br>5.48<br>7.07<br>16.15 | −475.1° |

TABLE I-continued

| Cmpd No. | Structure | Molecular Formula | Microanalysis | | | Optical Rotation $[\alpha]_D$ |
|---|---|---|---|---|---|---|
| | | | | Calcd | Found | |
| 8 | 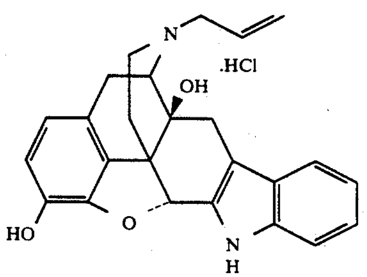 | $C_{25}H_{25}N_2O_3Cl$ + 1.5 $H_2O$ | C<br>H<br>N | 64.72<br>6.08<br>6.04 | 64.89<br>6.07<br>5.84 | −389.4° |
| 9 | 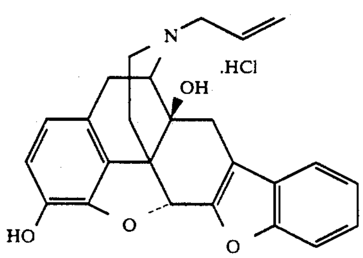 | $C_{25}H_{24}NO_4Cl$ + 0.3 $H_2O$ | C<br>H<br>N | 67.73<br>5.59<br>3.16 | 67.84<br>5.83<br>3.10 | −378.5° |
| 10 | 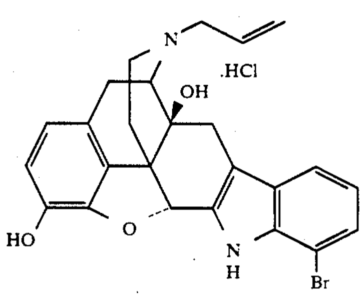 | $C_{25}H_{24}N_2O_3BrCl$ + 0.6 $H_2O$ | C<br>H<br>N | 57.01<br>4.82<br>5.32 | 56.96<br>4.74<br>5.32 | −419.6° |
| 11 | 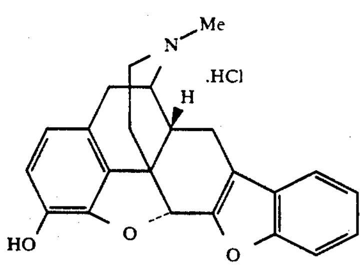 | $C_{23}H_{22}NO_3Cl$ + 1.0 $H_2O$ | C<br>H<br>N | 66.74<br>5.85<br>3.38 | 66.30<br>5.67<br>3.37 | −411.1° |
| 12 | 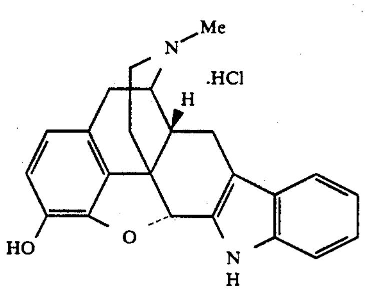 | $C_{23}H_{23}N_2O_2Cl$ + 1.0 $H_2O$ | C<br>H<br>N | 66.90<br>6.10<br>6.78 | 66.79<br>6.02<br>6.59 | −534.6° |

TABLE I-continued

| Cmpd No. | Structure | Molecular Formula | Microanalysis Calcd | Found | Optical Rotation $[\alpha]_D$ |
|---|---|---|---|---|---|
| 13 | 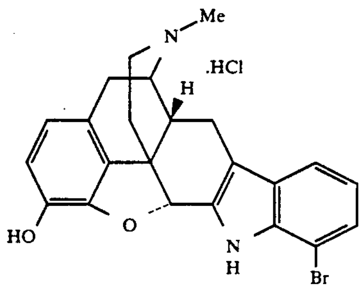 | $C_{23}H_{22}N_2O_2BrCl$ + 0.5 $H_2O$ | C 57.22<br>H 4.80<br>N 5.80 | 57.26<br>5.07<br>5.59 | −516.0° |
| 14 | 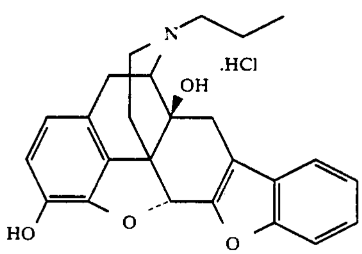 | $C_{25}H_{26}NO_4Cl$ + 0.7 $H_2O$ | C 66.35<br>H 6.10<br>N 3.10<br>Cl 7.83 | 66.47<br>6.03<br>3.13<br>7.86 | −376.2° |
| 15 | 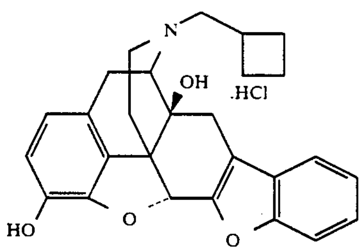 | $C_{27}H_{28}NO_4Cl$ + 0.4 $H_2O$ | C 68.53<br>H 6.14<br>N 2.96<br>Cl 7.49 | 68.49<br>6.05<br>3.00<br>7.28 | −400.9° |
| 16 | 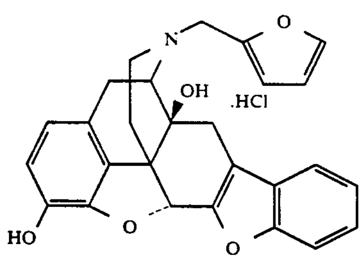 | $C_{27}H_{23}NO_5Cl$ + 0.8 HCl + 0.6 $H_2O$ | C 67.35<br>H 5.23<br>N 2.91<br>Cl 5.89 | 67.12<br>4.99<br>2.86<br>5.94 | −409.4° |
| 17 | 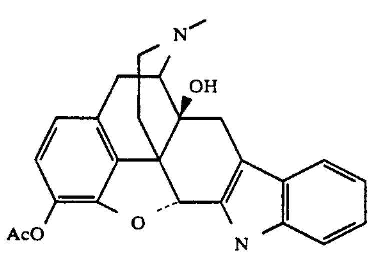 | $C_{25}H_{24}N_2O_4$ | C 72.10<br>H 5.81<br>N 6.73 | 72.06<br>5.87<br>6.59 | −350.5° |

TABLE I-continued

| Cmpd No. | Structure | Molecular Formula | Microanalysis Calcd | Found | Optical Rotation $[\alpha]_D$ |
|---|---|---|---|---|---|
| 18 | 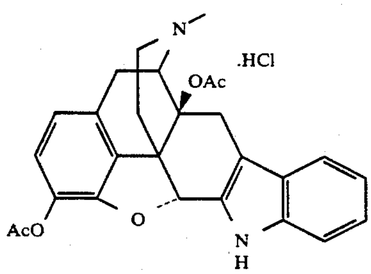 | $C_{27}H_{27}N_2O_5Cl$ + 0.8 $H_2O$ | C 63.66<br>H 5.66<br>N 5.50<br>Cl 6.96 | 63.69<br>5.44<br>5.36<br>7.10 | $-385.7°$ |
| 19 | 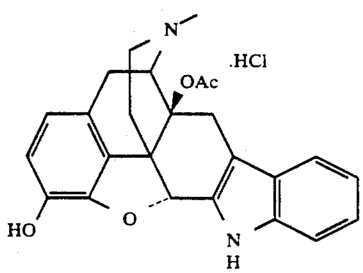 | $C_{25}H_{25}N_2O_4Cl$ + 0.1 HCl | C 65.76<br>H 5.54<br>N 6.14<br>Cl 8.54 | 65.76<br>5.56<br>5.93<br>8.74 | $-296.0°$ |

The biological activities of the compounds of this invention were determined by the following test procedures.

Description of Assays

(a) Writhing Assay

The Writhing Assay is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., *Arch. int. Pharmacodyn*, 267, 131–140 (1984); C. Vander Wende et al., *Fed. Proc.*, 15, 494 (1956); Koster et al., *Fed. Proc.*, 18, 412 (1959); and Witken et al., *J. Pharmacol. exp. Tger.*, 133, 400–408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table I below.

Charles River male albino mice, weighing 20 to 30 grams were used in this assay.

Thirty minutes after subcutaneous or intragastric administration to ten mice of either 10 mg or 30 mg per kilogram of body weight of a compound of the present invention ("test compound"), 0.1 mg per 10 g of body weight of a 0.025% w/v solution of PBQ was injected intraperitoneally into each mouse. Ten mice which were given saline in place of a test compound of the invention were used as a control group.

Five minutes later, each mouse was individually placed into a glass beaker for observation, and the number of writhes occurring during the following ten-minute period was counted.

A test compound was considered to be "active" in this assay (to have produced analgesia in a mouse) if, after the administration of the compound to the mouse, the number of writhes elicited by a mouse injected with PBQ was equal to, or less than, one-half the median number of writhes recorded for the saline-treated control group of mice that day, as described by Taber in "Predictive Value of Analgesic Assays in Mice and Rats," *Advances in Biochemical Psychopharmacology*, 8, 191 (1974).

The results for the particular compounds of the present invention analyzed in this assay, and discussed in the examples identified below which correspond thereto, were expressed in terms of the particular compounds being "active" or "inactive" in accordance with the conditions set forth above, and under the test criteria employed for this assay, and are presented in Table I below.

The standard initial screening doses of a test compound employed in this assay were 10 and/or 30 mpk per gram of body weight for both routes of administration.

The results obtained from this writhing assay are shown in Table I below, and correspond to the compound shown and described in the particular example identified below which corresponds thereto.

(b) Opiate Binding Assay

Compounds within the present invention were also evaluated in an opioid radioligand binding assay, which measures the affinity of opioids for specific opioid receptors in rat forebrain, by their ability to displace the binding of radiolabeled ligands specifically bound to $\mu$ and/or $\delta$ opioid receptors isolated from rat brain. Compounds which are determined to be active in this in vitro assay will generally have opioid-like effects in animals, including analgesia, unless they are not bioavailable.

A purified homogenate of receptor membranes was prepared from the brains of the rats according to the method described by K. J. Chang et al., "Multiple Opiate Receptors: Enkephalins and Morphine Bind to Receptors of Different Specificity," *J. Biol. Chem.*, 254, 2610-2618 (1979).

Male Charles River Sprague-Dawley albino rats weighing 150 to 300 g were stunned and decapitated. Their forebrains (minus the cerebellum and associated hindbrain) were quickly removed and rinsed in ice-cold 50 mM Tris buffer, pH 7.4, and homogenized in 20 volumes of buffer with a Polytron (Brinkman) at setting 6 for 30 seconds. The membranes were washed by centrifugation for 20 minutes at 30,000 × g, followed by resuspension to twice the original volume. The homogenate was incubated at 250 for 1 hour, followed by centrifugation as above.

The resulting homogenate was then assayed for protein content according to the method described by Itzhaki et al., "A Micro-Biuret Method for Estimating Proteins," *Anal. Biochem.*, 9, 401-410 (1961). The final pellet was resuspended to a protein concentration of 10 mg protein per mL (assuming 6% of wet weight is protein) and 4 mL aliquots were rapidly frozen in liquid $N_2$.

The binding of compounds within the invention to the rat brain opiate receptor membrane preparation containing either $\delta$ or $\mu$ opioid receptors was measured using a modification of the method of C. B. Pert et al., "Properties of Opiate Receptor Binding in Rat Brain," *Proc. Natl. Acad. Sci.*, 70, 2243-2247 (1972).

The opiate binding assays were conducted in triplicate at 37° C. in 50 mM TrisHCl buffer at pH 7.4 in a final volume of 1 mL, using varying concentrations of a compound of the invention. Each of three tubes contained 0.8 mL of homogenate containing approximately 1 mg/mL of protein. $^3$[H]-DAMGO (2.0 nM) and $^3$[H]-DSLET (1.0 nM) were used to label the $\mu$ and $\delta$ opiate rat brain receptors, respectively.

The "per cent displacement" of radiolabeled ligand ($^3$[H]-DAMGO for the $\mu$ receptors and $^3$[H]-DSLET for the $\delta$ receptors) bound to the $\mu$ or $\delta$ opioid receptors by a compound of the present invention was determined at different concentrations of the compound (10 $\mu$M, 1 $\mu$M, 100 nM and/or 1 nM). Because the radiolabeled ligand and the compound compete with each other for the opiate receptor binding sites, the greater the per cent of displacement of the bound radiolabeled ligand, the better the compound is in terms of its ability to bind to the opiate receptors and, thus, the more potent the compound is. "Specific binding" of a compound of the present invention to the $\mu$ or the $\delta$ opiate rat brain receptors was defined as the difference between total binding and that in the presence of 10 $\mu$M of levorphanol.

For those compounds which bound particularly well to the opiate receptors, the mean $IC_{50}$ value (that concentration of a particular compound which is required to have 50 per cent of the bound radiolabeled ligand displaced from the opiate receptors) was calculated (nM). $IC_{50}$ values were determined from log-logit plots of concentration vs. time response curves. Comparison of $IC_{50}$ values in this assay system provides a measure of the receptor specificity of the tested compounds.

Finally, for those compound for which a mean $IC_{50}$ value was calculated for both the $\mu$ and $\delta$ opioid receptors, the ratio of the mean $IC_{50}$ values for the $\mu$ and $\delta$ opioid receptors was determined. This ratio indicates how specific a particular compound is for the $\delta$ opioid receptors. Thus, if the ratio of the mean $IC_{50}$ values is 1.0, the compound is approximately equally potent for both the $\mu$ and the $\delta$ opioid receptors. The greater the number is above 1.0, the more specific the compound is for the $\delta$ opioid receptors.

The results obtained from this opiate binding assay are shown in Table II below, and correspond to the compound shown and described in the particular example identified below which corresponds thereto.

TABLE I

Data Generated from the PBO Writhing Assays

| EXAMPLE NUMBER | PBQ WRITHING ASSAY ($ED_{50}$ (mpk)) | |
|---|---|---|
| | I.G. | S.C. |
| II | 2.4 | 0.2 |
| III | inactive | 5/10 |
| IV | 2.2 | 6/10 |
| V | 2.7 | inactive |
| VI | inactive | 6/10 |
| VII | 2.3 | 0.9 |
| IX | 3.9 | 2.8 |
| X | 5/10* | 5/10* |
| XI | inactive | 2.0 |
| XIII | inactive | 4/10 |

*Number of mice in 10 exhibiting inhibition of writhing

TABLE II

Data Obtained from the Opiate Binding Assay

| Example Number | $IC_{50}$ | Percent Inhibition | Mean $IC_{50}$ $\mu/\delta$ Ratio |
|---|---|---|---|
| I | mu 152 | | 58 |
| I | delta 2.6 | | 58 |
| II | mu 93 | | 17 |
| II | delta 5.4 | | 17 |
| III | mu 550 | | 26 |
| III | delta 20.8 | | 26 |
| IV | mu 21,200 | | 446 |
| IV | delta 43.5 | | 446 |
| V | mu | 2% at 100 nm | N.C. |
| V | delta | 72% at 100 nm | N.C. |
| VI | delta | 11% 10 nm | N.C. |
| VI | | | |
| VII | mu 253 | | 25.3 |
| VII | delta 10 | | 25.3 |
| VIII | mu 99 | | 71 |
| VIII | delta 1.4 | | 71 |
| IX | mu 236 | | 1100 |
| IX | delta 0.21 | | 1100 |
| X | mu 3900 | | 350 |
| X | delta 11.1 | | 350 |
| XI | mu 24 | | 6.9 |
| XI | delta 3.5 | | 6.9 |
| XII | mu 58 | | 11.8 |
| XII | delta 4.9 | | 11.8 |
| XIII | mu 265 | | 5.1 |
| XIII | delta 52 | | 5.1 |
| XIV | mu 200 | | 26 |
| XIV | delta 7.7 | | 26 |
| XV | mu 690 | | 135 |
| XV | delta 5.1 | | 135 |
| XVI | mu 10.320 | | 10320 |
| XVI | delta 1 | | 10320 |
| XVII | mu 1305 | | 38 |
| XVII | delta 34 | | 38 |
| XVIII | mu | 72% at 100 nm | N.C. |
| XVIII | delta 66.4 | | N.C. |
| XIX | mu 769 | | 769 |
| XIX | delta 1 | | 769 |

N.C. = Not calculated

Dosage and Mode of Administration

The compounds of the present invention, and the pharmaceutical compositions comprising one or more of these compounds in combination with a pharmaceutically-acceptable carrier, are useful in treating pain in animals. A physician or veterinarian of ordinary skill in the art can readily determine whether or not a particular patient is in pain.

The pharmaceutical compositions of the present invention, which will typically comprise one or more of the compounds of Formula I as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. They may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are orally and parenterally, the most preferred mode of administration is orally.

Regardless of the route o administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the present invention will be that amount of the compound which is the lowest dose effective to produce a therapeutic effect. Such an effective dose will generally depend upon the factors described above. Generally, dosage levels in the range of from about 0.001 mg to about 10 g, more preferably from about 1 mg to about 1000 mg, of active compound (a compound of Formula I) per kilogram of body weight per day are administered to a mammalian patient. However, the total daily usage of the compounds of Formula I, or the pharmaceutical compositions comprising such compounds, will be determined by an attending physician or veterinarian within the scope of sound medical judgement.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfite, sodium metabisulfite, sodium sulfite and the like; (2) oil-soluble antioxidants, such as ascorbyl palmitate, butylated hydroxyanisole (BHA), butylated hydroxytoluene (BHT), propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which is the lowest dose effective to produce a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile, injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically-acceptable emulsions, microemulsions, solutions, suspensions, syrups and elixirs. In addition to the active ingredient (compound of Formula I), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving, dispersing or otherwise incorporating a compound of the present invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable dosage forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable media just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

What is claimed is:

1. A method for treating pain in a subject comprising administering to the subject a delta opioid selective agonist compound of the formula:

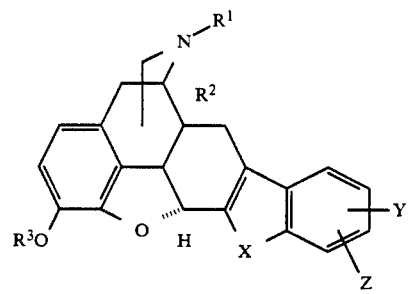

wherein:
R$^1$ represents hydrogen, C$_1$–C$_6$ alkyl, C$_3$–C$_6$ alkenyl, aralkyl or A–B wherein A represents C$_1$–C$_6$ alkylene and B represents C$_3$–C$_6$ cycloalkyl or substituted or unsubstituted aryl or heteroaryl;
R$^2$ represents hydrogen or —OR$^4$ wherein R$^4$ represents hydrogen, C$_1$–C$_6$ alkyl,

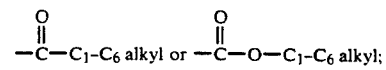

R$^3$ represents hydrogen, C$_1$–C$_6$ alkyl, aryl or aralkyl;
X is —NR, O or S wherein R represents hydrogen or C$_1$–C$_6$ alkyl; and Y and Z each independently represent hydrogen, halo, $C_1$-$C_6$ alkyl, $C_1$-$C_6$ alkoxy, $-NO_2$ or $-NH_2$, or Y and Z together form a phenyl ring, unsubstituted or substituted by one or more halo radicals or a pharmaceutically acceptable salt thereof.

2. The method of claim 1 in which $R^1$ is $C_1$-$C_6$ alkyl, $C_3$-$C_6$ alkenyl or A-B Wherein A is $C_1$-$C_6$ alkylene and B is $C_3$-$C_6$ cycloalkyl, phenyl or furyl;
$R^2$ is $OR^4$ wherein $R^4$ is $C_1$-$C_6$ alkyl;
$R^3$ is hydrogen or $C_1$-$C_6$ alkyl;
X is NH or O;
Y is hydrogen or halo; and
Z is hydrogen or halo or Y and Z together form a phenyl ring.

3. The method of claim 2 in which $R^1$ is methyl, propyl, propenyl or A-B wherein A is methylene or ethylene and B is cyclobutyl, phenyl or furyl;
$R^2$ is hydrogen, hydroxy or methoxy or $OR^4$ wherein $R^4$ is acyl;
$R^3$ is hydrogen or methyl;
X is NH or O;
Y is hydrogen or bromo; and
Z is hydrogen or bromo, or Y and Z together form a phenyl ring.

* * * * *

UNITED STATES PATENT AND TRADEMARK OFFICE
CERTIFICATE OF CORRECTION

PATENT NO. : 5,223,507

DATED : June 29, 1993

INVENTOR(S) : Dappen, et al.

It is certified that error appears in the above-indentified patent and that said Letters Patent is hereby corrected as shown below:

Abstract, line 3, reading "administrating" should read -- administering --.

Abstract, line 6, formula reading

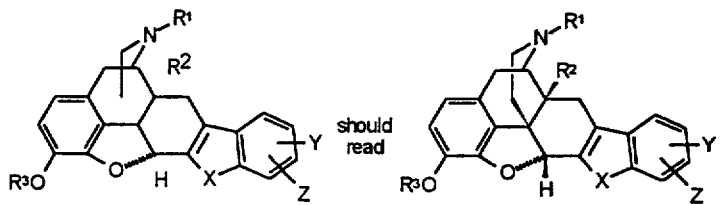

Column 1, line 39, reading "of the" should read -- of the formula --.

UNITED STATES PATENT AND TRADEMARK OFFICE
CERTIFICATE OF CORRECTION

PATENT NO. : 5,223,507
DATED : June 29, 1993
INVENTOR(S) : Dappen, et al.

It is certified that error appears in the above-indentified patent and that said Letters Patent is hereby corrected as shown below:

Column 1, line 41, formula reading

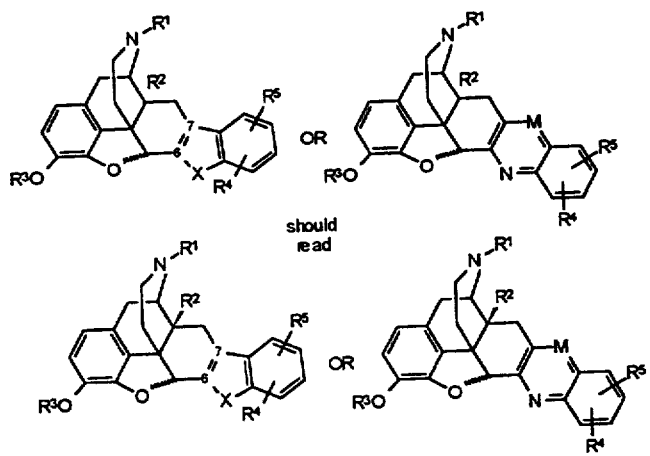

should read

Column 2, line 10, formula reading

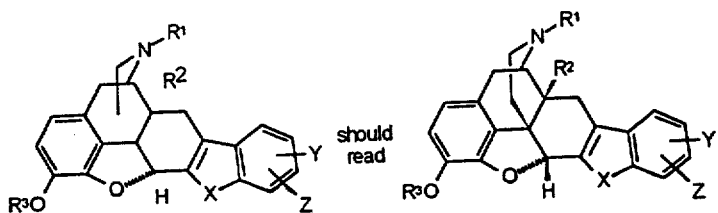

should read

Column 2, line 28, reading "hydrogen or $OR^4$ should read -- hydrogen or $-OR^4$ --.

Column 2, line 34, reading "X is NR," should read -- X is $-NR$, --.

UNITED STATES PATENT AND TRADEMARK OFFICE
CERTIFICATE OF CORRECTION

PATENT NO. : 5,223,507
DATED : June 29, 1993
INVENTOR(S) : Dappen, et al.

It is certified that error appears in the above-indentified patent and that said Letters Patent is hereby corrected as shown below:

Column 2, line 37, reading "NO₂ or NH₂" should read -- -NO₂ or -NH₂ --.

Column 4, line 18, reading "Description of Invention" should read -- (2) Description of Invention --.

Column 6, line 5, formula reading

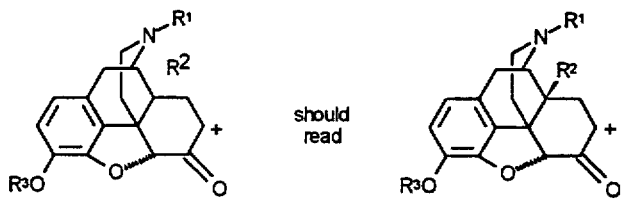

Column 6, line 25, formula reading

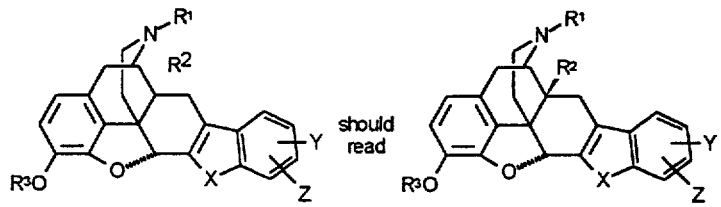

UNITED STATES PATENT AND TRADEMARK OFFICE
CERTIFICATE OF CORRECTION

PATENT NO. : 5,223,507
DATED : June 29, 1993
INVENTOR(S) : Dappen, et al.

It is certified that error appears in the above-indentified patent and that said Letters Patent is hereby corrected as shown below:

Column 6, line 35, formula reading

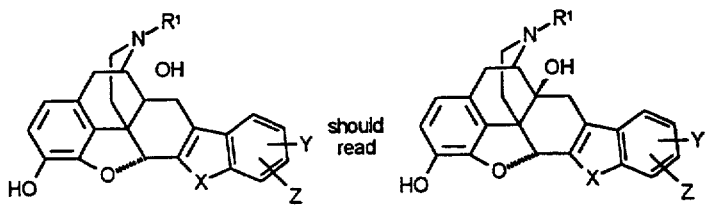

Column 6, line 50, formula reading

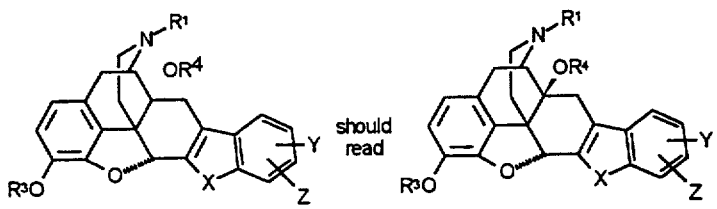

Column 7, line 56, reading "(2 x 50 mL)," should read -- (2 x 150 mL), --.

Column 8, line 15, reading "6.6I" should read -- 6.61 --.

Column 9, line 61, reading "2,4 dibromophenylhydrazine" should read -- 2,4-dibromophenylhydrazine --.

Column 13, line 16, reading "1,8αβ-9H)" should read -- 1,8αβ(9H) --.

UNITED STATES PATENT AND TRADEMARK OFFICE
CERTIFICATE OF CORRECTION

PATENT NO. : 5,223,507
DATED : June 29, 1993
INVENTOR(S) : Dappen, et al.

It is certified that error appears in the above-indentified patent and that said Letters Patent is hereby corrected as shown below:

Column 13, line 20, reading "17 Was" should read -- 17 was --.

Column 13, line 31, reading "b silica gel" should read -- by silica gel --.

Column 16, line 10, reading "H 5.47" should read -- H 5.74 --.

Column 21, line 45, reading "Tger.," should read -- Ther., --.

Column 23, line 37, reading "TrisHCl" should read -- Tris/HCl --.

Column 30, line 42, formula reading

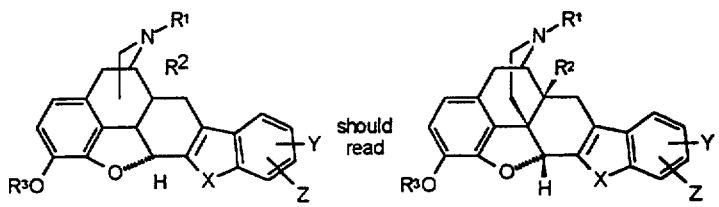

Column 31, line 7, reading "A-B Wherein" should read -- A-B wherein --.

Column 31, line 12, reading "X is NH or O" should read -- X is -NH or O --.

UNITED STATES PATENT AND TRADEMARK OFFICE
CERTIFICATE OF CORRECTION

PATENT NO. : 5,223,507
DATED : June 29, 1993
INVENTOR(S) : Dappen, et al.

It is certified that error appears in the above-indentified patent and that said Letters Patent is hereby corrected as shown below:

Column 32, line 6, reading "$R^2$ is hydrogen, hydroxy" should read -- $R^2$ is hydroxy --.

Column 32, line 9, reading X is NH or O" should read -- X is -NH or O --.

Signed and Sealed this

Thirteenth Day of December, 1994

BRUCE LEHMAN

*Attest:*

*Attesting Officer*     *Commissioner of Patents and Trademarks*